United States Patent [19]

Bigg et al.

[11] Patent Number: 5,034,541

[45] Date of Patent: Jul. 23, 1991

[54] METHOD OF PREPARING 1-PHENYL-1-DIETHYLAMINOCARBONYL-2-PHTHALIMIDOMETHYL-CYCLOPROPANE-Z

[75] Inventors: Dennis C. H. Bigg; Patrick Lesimple, both of Castres, France

[73] Assignee: Pierre Fabre Medicament, Castres, France

[21] Appl. No.: 457,352

[22] Filed: Dec. 27, 1989

[30] Foreign Application Priority Data

Dec. 28, 1988 [FR] France .................. 88 17326

[51] Int. Cl.$^5$ .................. C07D 209/48; C07D 307/32
[52] U.S. Cl. .................. 548/477; 548/473; 549/302; 564/161; 564/171
[58] Field of Search .............. 564/164, 134, 171, 161; 548/477, 473; 549/302

[56] References Cited

FOREIGN PATENT DOCUMENTS

| 68998 | 1/1983 | European Pat. Off. ............ 564/164 |
| 200638 | 11/1986 | European Pat. Off. ............ 564/164 |
| 2581060 | 4/1985 | France ................. 564/164 |

OTHER PUBLICATIONS

Bonnaud et al, Chem. Abst. 107-58662m (1987).
Birkofer, et al., Chemische Berichte Jahrg. 93, 1960, pp. 2282-2284.

*Primary Examiner*—Cecilia Shen
*Attorney, Agent, or Firm*—Gordon W. Hueschen

[57] ABSTRACT

A method of preparing 1-phenyl-1-diethylaminocarbonyl-2-phthalimidomethyl-cyclopropane-Z and key intermediates therefor are disclosed.

This method is characterized by the following successive steps:

opening of the 1-phenyl-2-oxo-3-oxa-bicyclo(3:1:0)-hexane by diethylamine or a tertiary amine with the aid of a Lewis acid/amine complex:

the 1-phenyl-1-diethylaminocarbonyl-2-hydroxymethyl-cyclopropane-Z thus obtained is converted into a 2-chlorinated derivative by the action of a chlorination reagent such as thionyl chloride; and the 1-phenyl-1-diethylaminocarbonyl-2-chloromethyl-cyclopropane-Z is reacted with a phthalimide salt in an organic solvent to produce the 1-phenyl-1-diethylaminocarbonyl-2-phthaliumidomethyl-cyclopropane-Z.

14 Claims, No Drawings

METHOD OF PREPARING 1-PHENYL-1-DIETHYLAMINOCARBONYL-2-PHTHALIMIDOMETHYL-CYCLOPROPANE-Z

FIELD OF INVENTION

The present invention, made at the Pierre Fabre Medicament Research Center, concerns a new method of preparing 1-phenyl-1-diethylaminocarbonyl-2-phthalimidomethyl-cyclopropane-Z, corresponding to Formula I, and important key intermediates in the process.

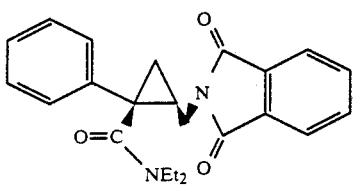

I

BACKGROUND OF THE INVENTION AND PRIOR ART

The 1-phenyl-1-diethylaminocarbonyl-2-phthalimidomethyl-cyclopropane-Z serves as an important precursor for the manufacture of MILNACIPRAN (D.C.I.), a drug useful in the treatment of depression and which has Formula II

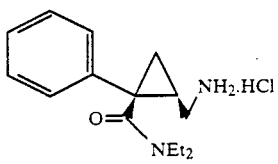

II from which it is prepared by splitting off the phthalimido group and conversion to the hydrochloride salt, advantageously using an alkanolamine such as ethanolamine and hydrochlorinating in conventional manner according to EP published application 0200638 published Nov. 5, 1986.

In the prior art, illustrated by F 2,581,059, the compound of Formula I is prepared in several steps from 1-phenyl-2-oxo-3-oxa-bicyclo(3:1:0)hexane in a yield of about 50%.

OBJECTS OF THE INVENTION

The object of the new method is to prepare a compound of Formula I in excellent yield and purity in accordance with the following scheme, proceeding through important and novel key intermediates.

First step:

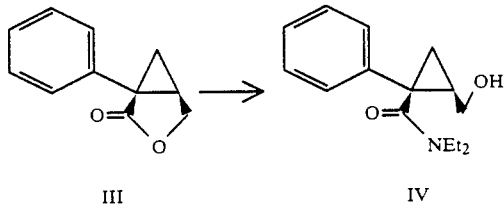

III → IV

Second step:

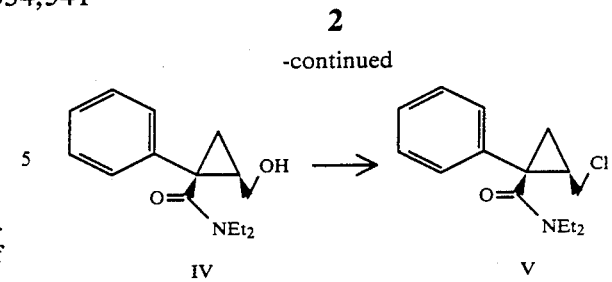

IV → V

Third step:

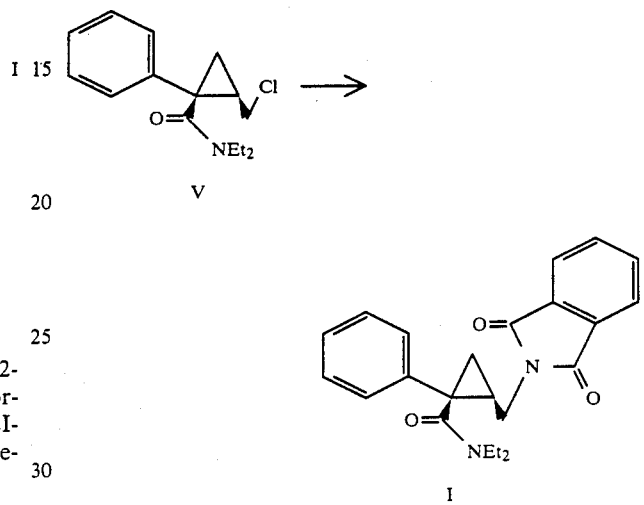

V → I

Other objects of the invention will be obvious to one skilled in the art and still others will become apparent upon reading the following specification and claims.

SUMMARY OF THE INVENTION

The invention, then, includes the following aspects, inter alia, singly or in combination:

A method of preparing 1-phenyl-1-diethylaminocarbonyl-2-phthalimidomethyl-cyclopropane-Z comprising the following successive steps:

opening of the 1-phenyl-2-oxo-3-oxa-bicyclo(3:1:0)hexane lactone using diethylamine with the aid of a Lewis acid/amine complex, converting the 1-phenyl-1-diethylaminocarbonyl-2-hydroxymethyl-cyclopropane-Z thus obtained into its 2-chloro derivative by the action of a chlorination reagent; and converting the 1-phenyl-1-diethylaminocarbonyl-2-chloromethyl-cyclopropane-Z thus obtained into the compound I by reaction with a phthalimide salt in an organic solvent; such a method wherein the Lewis acid is aluminum chloride; such a method wherein the amine of the aluminum chloride-amine complex is diethylamine or a tertiary amine; such a method wherein at least one equivalent of the aluminum chloride-amine complex is employed; such a method wherein at least one equivalent of diethylamine is employed; such a method wherein the solvent employed for the opening of the lactone ring is selected from dichloroethane and dichloromethane; such a method wherein the reaction temperature is between about 10° C. and 30° C. for the opening of the lactone ring; such a method wherein thionyl chloride is used in the second step to effect the transformation of the alcohol into its chlorinated derivative; such a method wherein the reaction of the alcohol with thionyl chloride is carried out at a temperature between about 10° C. and 50° C.; such a method wherein the reaction betwen the alcohol and the thionyl chloride is carried out in an organic solvent; such a method wherein the solvent is dichloroethane or dichloromethane; such a method wherein the phthalimide salt employed is potassium phthalimide; such a method wherein the reaction between the chlorinated compound and the potassium phthalimide is carried out in an organic solvent selected from dimethylformamide, dimethylacetamide, methylpyrrolidone, toluene, and dichloroethane; and such a method wherein the reaction between the chlorinated compound and the potassium phthalimide is carried out at a temperature between about 80° C. and 120° C.; as well as the important key intermediates 1-phenyl-1-diethylaminocarbonyl-2-hydroxymethyl-cyclopropane-Z and 1-phenyl-1-diethylaminocarbonyl-2-chloromethyl-cyclopropane-Z.

THE INVENTION

The first step of the process consists of opening the lactone of Formula III with diethylamine by means of a Lewis acid/amine complex in the presence of a suitable organic solvent such as dichloroethane or dichloromethane.

The Lewis acid employed is preferably aluminum chloride, and the amine of the complex is either diethylamine or a tertiary amine. Among suitable tertiary amines, mention may be made, by way of nonlimitative example, of triethylamine, diisopropylethylamine, N,N-diethylaniline, N,N-dimethylbenzylamine, N-methylpiperidine, N-methylmorpholine, N,N'-dimethylpiperazine, and hexamethylene tetramine.

The reaction is most advantageously carried out with at least one equivalent of the aluminum chlorideamine complex and at least one equivalent of the diethylamine or tertiary amine.

The reaction is advantageously carried out at a temperature between about 10° C. and 30° C.

The yield in this first step is almost quantitative, which makes it possible to obtain a crude product of excellent quality which can serve directly for the following step. Further purification can, however, be carried out, if necessary, by known means such as chromatography or recrystallization, for instance, of a dichloromethane/diisopropylether mixture.

In the second reaction step, the 1-phenyl-1-diethylaminocarbonyl-2-hydroxymethyl-cyclopropane-Z of Formula IV is converted into 1-phenyl-1-diethylaminocarbonyl-2-chloromethyl-cyclopropane-Z of Formula V by means of a chlorination reagent such as thionyl chloride, used preferably in stoichiometric excess.

The reaction is advantageously carried out at a temperature between about 10° C. and 50° C., snd preferably at room temperature, in an inert solvent such as dichloroethane or dichloromethane.

The product obtained is of very good quality and can serve directly for the following step.

In the third step, the chlorinated derivative of Formula V is reacted with a phthalimide salt, preferably the potassium salt, in an inert organic solvent such as dimethylformamide, dimethylacetamide, methylpyrrolidone, toluene, or dichloroethane.

The reaction temperature is preferably between about 80° C. and 120° C.

The 1-phenyl-1-diethylaminocarbonyl-2-phthalimidomethyl-cyclopropane-Z of Formula I is obtained in a high yield, and the product is of excellent purity.

The yield in each step and the purity of the products obtained are such that the method of the invention permits an economic industrial synthesis of surprising efficacy.

DETAILED DESCRIPTION OF THE INVENTION

The following Examples illustrate the invention without, however, limiting its scope.

EXAMPLE 1

1-Phenyl-1-diethylaminocarbonyl-2-hydroxymethylcyclopropane-Z (Formula IV)
Method with AlCl3-Et2NH complex 40 g of aluminum chloride are added, with agitation, to a solution of 50 g of 1-phenyl-2-oxo-3-oxa-bicyclo (3:1:0)hexane in 500 ml of dichloroethane.

The flask is cooled, and 63 ml of diethylamine dissolved in dichloroethane are introduced. Agitation is continued for 0.5 hour, followed by hydrolysis with 1 liter of cold water.

The organic phase is washed with water and brine and finally dried over sodium sulfate.

The organic phase which has thus been dried is evaporated to dryness, obtaining 67.9 g of the compound of Formula IV in the form of cream crystals.

Yield 95%
Purity (HPLC): 97%
Melting point: 54°–55° C.

EXAMPLE 2

1-Phenyl-1-diethylaminocarbonyl-2-hydroxymethylcyclopropane-Z (Formula IV)
Method with $AlCl_3$-$Et_3N$ complex 4.2 ml of triethylamine are added, with agitation and cooling, to a suspension of 3.5 grams of aluminum chloride in 20 ml of dichloroethane.

When the reaction medium is homogeneous, 3.5 grams of the lactone dissolved in 20 ml of dichloroethane are added, whereupon 2.5 ml of diethylamine are added.

The reaction mixture is agitated for three hours at room temperature and then treated in the manner described in Example 1 to produce 4.35 grams of the compound of Formula IV in the form of cream crystals.

Yield 90%
Melting point: 54°–55° C.

EXAMPLE 3

1-Phenyl-1-diethylaminocarbonyl-2-hydroxymethylcyclopropane-Z (Formula IV)
Method with $AlCl_3$-N-methylmorpholine complex In a manner similar to that described in Example 2, but using N-methylmorpholine, 4.3 grams of the compound of Formula IV are obtained in the form of cream crystals.

Yield 87%
Melting point: 54°–55° C.

EXAMPLE 4

1-Phenyl-1-diethylaminocarbonyl-2-chloromethylcyclopropane-Z (Formula V)

To a solution of 15.5 grams of 1-phenyl-1-diethylaminocarbonyl-2-hydroxymethyl-cyclopropane-Z (Formula IV) in 100 ml of dichloroethane, 5 ml of thionyl chloride are added. The reaction mixture is agitated at room temperature for 0.25 hour and concentrated to dryness.

The syrup obtained is taken up in 100 ml of dichloroethane and washed in succession with water, a solution of sodium bicarbonate, and then again with water.

The organic phase is dried over sodium sulfate and, after evaporation, 16.2 grams of the compound of Formula V are obtained in the form of an oil.

Yield 97%
CCM (silica gel GF 245 Merck)
RF: 0.8 (hexane/ethyl acetate : ⅔)
IR: 1635 cm$^{-1}$ (C(O)NEt$_2$)

EXAMPLE 5

1-Phenyl-1-diethylaminocarbonyl-2-phthalimidomethylcyclopropane-Z (Formula I)

10 grams of 1-phenyl-1-diethylaminocarbonyl-2-chloromethyl-cyclopropane-Z (Formula V) are dissolved in 20 ml of DMF, whereupon 8.7 grams of potassium phthalimide are added and the reaction mixture is heated for three hours at 110° C.

The reaction product is allowed to cool and the solution is poured into 150 ml of water. After filtration, washing in water, and drying, 13.5 grams of the compound of Formula I are obtained in the form of white crystals.

Yield 95%
Purity (HPLC): 99%
Melting point: 131°-132° C.

EXAMPLE 6

1-Phenyl-1-diethylaminocarbonyl-2-phthalimidomethylcyclopropane-Z (Formula I)
Method without isolation of the intermediates.

A 20-liter reactor is charged with 3.5 liters of dichloroethane and 510 grams of aluminum chloride. A solution of 765 ml of diethylamine in 0.8 liters of dichloroethane is added with cooling and agitation. When the mixture is homogeneous, 500 grams of 1-phenyl-2-oxo-3-oxa-bicyclo(3:1:0)hexane dissolved in 1.7 liters of dichloroethane are added.

The suspension which forms is agitated for two hours at room temperature and then hydrolyzed by the addition of 9 liters of water. After settling, the aqueous phase is extracted with dichloroethane and the organic phases are combined and washed with 8 liters of water before being dried by azeotropic distillation.

The solution of 1-phenyl-1-diethylaminocarbonyl-2-hydroxymethyl-cyclopropane-Z (Formula IV) thus obtained is concentrated to approximately 2.5 liters and used directly in the following step.

The solution of the compound of Formula IV in dichloroethane obtained in the above manner is charged into a 6-liter reactor and 215 ml of thionyl chloride added, while maintaining the temperature at about 25° C. When the addition of thionyl chloride is complete, the reaction medium is concentrated under vacuum, 0.5 liters of toluene are added, and distillation is effected to remove traces of hydrochloric acid.

Then three liters of dimethylformamide are added to the 1-phenyl-1-diethylaminocarbonyl-2-chloromethyl-cyclopropane-Z (Formula V) thus obtained, followed by 678 grams of potassium phthalimide. The reaction mixture is heated, with agitation, for two hours at 100°-110° C., whereafter the mixture of reaction products is allowed to cool and then poured into 15 liters of water with agitation.

The creamy-white crystals obtained are filtered and washed with water, whereupon the cake is made into a paste using a minimum amount of di-isopropyl ether. After filtration and drying, 980 grams of 1-phenyl-1-diethylaminocarbonyl-2-phthalimidomethyl-cyclopropane-Z (Formula I) are obtained in the form of white crystals.

Overall yield from the three steps: 91%
Purity (HPLC): 98%
Boiling point: 131°-132° C.

It is therefore seen that the present invention provides a novel and highly advantageous method for the preparation of the compound of Formula I (1-phenyl-1-diethylaminocarbonyl-2-phthalimidomethyl-cyclopropane-Z) from the compound of Formula III (1-phenyl-2-oxo-3-oxa-bicyclo(3:1:0)hexane lactone) in a unique three (3) step procedure, which may be conducted with or without isolation of the key intermediates of Formula IV and V, as well as these novel key intemediates themselves, all having the unpredictable and highly advantageous characteristics and effects as more fully set forth in the foregoing.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope which can be legally accorded to the appended claims.

We claim:
1. A method of preparing 1-phenyl-1-diethylaminocarbonyl-2-phthalimidomethyl-cyclopropane-Z of Formula I:

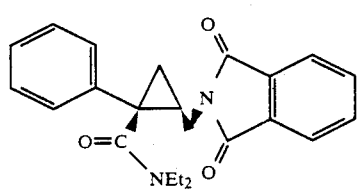

comprising the following successive steps:
opening of the 1-phenyl-2-oxo-3-oxa-bicyclo(3:1:0-)hexane lactone of Formula III using diethylamine with the aid of a Lewis acid/amine complex:

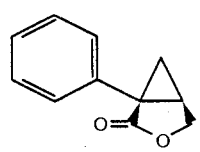

converting the 1-phenyl-1-diethylaminocarbonyl-2-hydroxymethyl-cyclopropane-Z of Formula IV thus obtained:

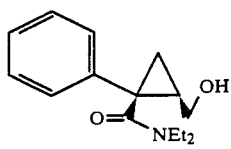

IV into its 2-chloro derivative by the action of a chlorination reagent; and converting the 1-phenyl-1-diethylaminocarbonyl-2-chloromethyl-cyclopropane-Z of Formula V thus obtained:

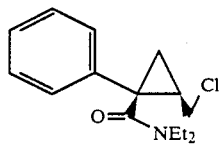

V into a compound of Formula I by reaction with a phthalimide salt in an organic solvent.

2. A method according to claim 1, wherein the Lewis acid is aluminum chloride.

3. A method according to claim 2, wherein the amine of the aluminum chloride-amine complex is diethylamine or a tertiary amine.

4. A method according to either of claims 2 and 3, wherein at least one equivalent of the aluminum chloride-amine complex is employed.

5. A method according to any of claims 1 to 4, wherein at least one equivalent of diethylamine is employed.

6. A method according to any of claims 1 to 5, wherein the solvent employed for the opening of the lactone of Formula III is selected from dichloroethane and dichloromethane.

7. A method according to any of claims 1 to 6, wherein the reaction temperature is between about 10° C. and 30° C. for the opening of the lactone of Formula III.

8. A method according to any of claims 1 to 7, wherein thionyl chloride is used in the second step to effect the transformation of the alcohol of Formula IV into the chlorinated derivative of Formula V.

9. A method according to claim 8, wherein the reaction of the alcohol of Formula IV with thionyl chloride is carried out at a temperature between about 10° C. and 50° C.

10. A method according to claim 9, wherein the reaction between the alcohol of Formula IV and the thionyl chloride is carried out in an organic solvent.

11. A method according to claim 10, wherein the solvent is dichloroethane or dichloromethane.

12. A method according to any of claims 1 to 11, wherein the phthalimide salt employed is potassium phthalimide.

13. A method according to claim 12, wherein the reaction between the chlorinated compound of Formula V and the potassium phthalimide is carried out in an organic solvent selected from dimethylformamide, dimethylacetamide, methylpyrrolidone, toluene, and dichloroethane.

14. A method according to claim 13, wherein the reaction between the chlorinated compound of Formula V and the potassium phthalimide is carried out at a temperature between about 80° C. and 120° C.

* * * * *